US007572587B2

(12) United States Patent
Rupar et al.

(10) Patent No.: US 7,572,587 B2
(45) Date of Patent: *Aug. 11, 2009

(54) BACILLUS THURINGIENSIS CRYET29 COMPOSITIONS TOXIC TO COLEOPTERAN INSECTS AND CTENOCEPHALIDES SPP

(75) Inventors: Mark J. Rupar, Wilmington, DE (US); William P. Donovan, Levittown, PA (US); Yuping Tan, Fremont, CA (US); Annette C. Slaney, Hamilton Square, NJ (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/712,704

(22) Filed: Mar. 1, 2007

(65) Prior Publication Data

US 2007/0163000 A1 Jul. 12, 2007

Related U.S. Application Data

(60) Continuation of application No. 10/767,605, filed on Jan. 29, 2004, now Pat. No. 7,186,893, which is a division of application No. 10/386,972, filed on Mar. 12, 2003, now Pat. No. 6,686,452, which is a division of application No. 09/611,216, filed on Jul. 6, 2000, now Pat. No. 6,537,756, which is a division of application No. 08/721,259, filed on Sep. 26, 1996, now Pat. No. 6,093,695.

(51) Int. Cl.
*C12Q 1/68* (2006.01)
*C07H 21/04* (2006.01)
(52) U.S. Cl. .......................... 435/6; 536/23.1
(58) Field of Classification Search ................ 536/23.1
See application file for complete search history.

(56) References Cited

U.S. PATENT DOCUMENTS

| 4,547,360 | A | 10/1985 | Perlberg | 424/15 |
|---|---|---|---|---|
| 5,173,409 | A | 12/1992 | English | 435/71.1 |
| 5,187,091 | A | 2/1993 | Donovan et al. | 435/240.4 |
| 5,264,364 | A | 11/1993 | Donovan et al. | 435/252.5 |
| 5,276,269 | A | 1/1994 | Raikhel | 800/205 |
| 5,338,544 | A | 8/1994 | Donovan | 424/93.2 |
| 5,449,681 | A | 9/1995 | Wickiser | 514/366 |
| 5,482,852 | A | 1/1996 | Yoder et al. | 435/172.3 |
| 5,508,468 | A | 4/1996 | Lundquist et al. | 800/205 |
| 5,550,318 | A | 8/1996 | Adams et al. | 800/205 |
| 6,537,756 | B1 | 3/2003 | Rupar et al. | 435/6 |
| 6,593,114 | B1 * | 7/2003 | Kunsch et al. | 435/91.41 |

FOREIGN PATENT DOCUMENTS

| WO | WO9116433 A | 10/1991 |
|---|---|---|
| WO | WO94/13785 | 6/1994 |
| WO | WO94/16079 | 7/1994 |
| WO | WO95/02693 | 1/1995 |
| WO | WO9618302 A | 6/1996 |
| WO | WO98/13497 | 4/1998 |

OTHER PUBLICATIONS

Baum and Malvar, "Regulation of insecticidal crystal protein production in *Bacillus thuringiensis*," *Molecular Microbiology*, 18(1):1-12 (1995).
Chilcott and Ellar, "Comparative Toxicity of *Bacillus thuringiensis* var. *israelensis* Crystal Proteins in vivo and in vitro," *J. of General Microbiology*, 134:2551-2558 (1988).
Dhir et al., "Regeneration of transformed shoots from electroporated soybean (*Glycine max* (L.) Merr.) protoplasts," *Plant Cell Reports*, 10:97-101 (1991).
Donovan et al., "Characterization of Two Genes Encoding *Bacillus thuringiensis* Insecticidal Crystal Proteins Toxic to *Coleoptera* Species," *Applied and Environmental Microbiology*, 58(12):3921-3927 (Dec. 1992).
Earp and Ellar, "*Bacillus thuringiensis* var. *morrisoni* strain PG14: nucleotide sequence of a gene encoding a 27kDa crystal protein," *Nucleic Acids Research*, 15(8):3619 (1987).
Knowles et al., "A broad-spectrum cytolytic toxin from *Bacillus thuringiensis* var. *kyushuensis*," *Proc. R. Soc. Lond. B*, 248:1-7 (1992).
Koni and Ellar, "Cloning and Characterization of a Novel *Bacillus thuringiensis* Cytolytic Delta-Endotoxin," *J. Mol. Biol.*, 229:319-327 (1993).
Ward et al., "Cloning and expression in *Escherichia coli* of the insecticidal δ-endotoxin gene of *Bacillus thuringiensis* var. *israelensis*," *FEBS*, 175(2):377-382 (Oct. 1984).

(Continued)

*Primary Examiner*—Gary Benzion
*Assistant Examiner*—Cynthia B Wilder

(74) *Attorney, Agent, or Firm*—Timothy K. Ball, Esq.; Howrey LLP

(57) ABSTRACT

Disclosed is a novel δ-endotoxin, designated CryET29, that exhibits insecticidal activity against siphonapteran insects, including larvae of the cat flea (*Ctenocephalides felis*), as well as against coleopteran insects, including the southern corn rootworm (*Diabrotica undecimpunctata*), western corn rootworm (*D. virgifera*), Colorado potato beetle (*Leptinotarsa decemlineata*), Japanese beetle (*Popillia japonica*), and red flour beetle (*Tribolium castaneum*). Also disclosed are nucleic acid segments encoding CryET29, recombinant vectors, host cells, and transgenic plants comprising a cryET29 DNA segment. Methods for making and using the disclosed protein and nucleic acid segments are disclosed as well as assays and diagnostic kits for detecting cryET29 and CryET29 sequences in vivo and in vitro.

6 Claims, 2 Drawing Sheets

OTHER PUBLICATIONS

Ward and Ellar, "*Bacillus thuringiensis* var. *israelensis* δ-Endotoxin Nucleotide Sequence and Characterization of the Transcripts in *Bacillus thuringiensis* and *Escherichia coli*," *J. Mol. Biol.*, 191:1-11 (1986).

Ely, S.: "The engineering of plants to express *Bacillus thuringiensis* delta-endotoxins"; Entwistle, E. et al. (Eds.): '*Bacillus thuringiensis*, an Environmental Biopesticide: Theory and Practice' 1993, GB, Chichester, Wiley & Sons, pp. 105-124, XP002054693.

* cited by examiner

```
          10        20        30        40        50        60
           |         |         |         |         |         |
GAAACAGTATGAAAGGGGTAATTTTATATGTTCTTTAATCGCGTTATTACATTAACAGTA
                  METPhePheAsnArgValIleThrLeuThrVal 70        80        90       100       110       120
           |         |         |         |         |         |
CCATCTTCAGATGTGGTTAATTATAGTGAAATTTATCAGGTAGCTCCACAATATGTGAAT
ProSerSerAspValValAsnTyrSerGluIleTyrGlnValAlaProGlnTyrValAsn 130       140       150       160       170       180
           |         |         |         |         |         |
CAAGCTCTTACGCTAGCTAAATATTTCCAAGGAGCAATTGATGGTTCAACATTACGTTTT
GlnAlaLeuThrLeuAlaLysTyrPheGlnGlyAlaIleAspGlySerThrLeuArgPhe 190       200       210       220       230       240
           |         |         |         |         |         |
GATTTTGAAAAAGCCTTACAAATTGCAAATGATATTCCACAGGCAGCAGTGGTAAACACT
AspPheGluLysAlaLeuGlnIleAlaAsnAspIleProGlnAlaAlaValValAsnThr 250       260       270       280       290       300
           |         |         |         |         |         |
TTAAATCAAACTGTGCAGCAAGGTACAGTCCAAGTATCAGTGATGATAGACAAGATTGTA
LeuAsnGlnThrValGlnGlnGlyThrValGlnValSerValMETIleAspLysIleVal 310       320       330       340       350       360
           |         |         |         |         |         |
GACATTATGAAGAATGTATTATCTATTGTAATTGATAACAAAAAGTTTTGGGATCAGGTA
AspIleMETLysAsnValLeuSerIleValIleAspAsnLysLysPheTrpAspGlnVal
```

FIG. 1A

```
              370       380       390       400       410       420
               |         |         |         |         |         |
        ACAGCTGCTATTACAAATACATTCACAAATCTAAATTCGCAAGAAAGCGAAGCATGGATT
        ThrAlaAlaIleThrAsnThrPheThrAsnLeuAsnSerGlnGluSerGluAlaTrpIle 430       440       450       460       470       480
               |         |         |         |         |         |
        TTTTATTACAAAGAAGATGCACATAAAACTAGTTACTATTATAATATCTTATTTGCTATA
        PheTyrTyrLysGluAspAlaHisLysThrSerTyrTyrTyrAsnIleLeuPheAlaIle 490       500       510       520       530       540
               |         |         |         |         |         |
        CAGGATGAGGAAACAGGTGGGGTAATGGCGACATTACCGATTGCATTTGATATTAGTGTA
        GlnAspGluGluThrGlyGlyValMETAlaThrLeuProIleAlaPheAspIleSerVal 550       560       570       580       590       600
               |         |         |         |         |         |
        GATATTGAAAAGAAAAGGTTCTATTTGTTACTATCAAGGATACTGAAAATTATGCGGTT
        AspIleGluLysGluLysValLeuPheValThrIleLysAspThrGluAsnTyrAlaVal 610       620       630       640       650       660
               |         |         |         |         |         |
        ACAGTAAAAGCTATTAATGTAGTACAAGCACTTCAATCTTCCCGAGATTCAAAAGTTGTA
        ThrValLysAlaIleAsnValValGlnAlaLeuGlnSerSerArgAspSerLysValVal 670       680       690       700       710       720
               |         |         |         |         |         |
        GATGCTTTTAAATCGCCACGTCACTTACCTAGAAAAAGACATAAAATTTGTAGTAACTCT
        AspAlaPheLysSerProArgHisLeuProArgLysArgHisLysIleCysSerAsnSer

TAA
```

FIG. 1B

SEQUENCE LISTING

<160> NUMBER OF SEQ ID NOS: 4

<210> SEQ ID NO 1
<211> LENGTH: 693
<212> TYPE: DNA
<213> ORGANISM: Bacillus thuringiensis
<220> FEATURE:
<221> NAME/KEY: CDS
<222> LOCATION: (1)..(693)

<400> SEQUENCE: 1

```
atg ttc ttt aat cgc gtt att aca tta aca gta cca tct tca gat gtg      48
Met Phe Phe Asn Arg Val Ile Thr Leu Thr Val Pro Ser Ser Asp Val
1               5                   10                  15 gtt aat tat agt gaa att tat cag gta gct cca caa tat gtg aat caa      96
Val Asn Tyr Ser Glu Ile Tyr Gln Val Ala Pro Gln Tyr Val Asn Gln
            20                  25                  30 gct ctt acg cta gct aaa tat ttc caa gga gca att gat ggt tca aca     144
Ala Leu Thr Leu Ala Lys Tyr Phe Gln Gly Ala Ile Asp Gly Ser Thr
        35                  40                  45 tta cgt ttt gat ttt gaa aaa gcc tta caa att gca aat gat att cca     192
Leu Arg Phe Asp Phe Glu Lys Ala Leu Gln Ile Ala Asn Asp Ile Pro
    50                  55                  60 cag gca gca gtg gta aac act tta aat caa act gtg cag caa ggt aca     240
Gln Ala Ala Val Val Asn Thr Leu Asn Gln Thr Val Gln Gln Gly Thr
65                  70                  75                  80 gtc caa gta tca gtg atg ata gac aag att gta gac att atg aag aat     288
Val Gln Val Ser Val Met Ile Asp Lys Ile Val Asp Ile Met Lys Asn
                85                  90                  95 gta tta tct att gta att gat aac aaa aag ttt tgg gat cag gta aca     336
Val Leu Ser Ile Val Ile Asp Asn Lys Lys Phe Trp Asp Gln Val Thr
            100                 105                 110 gct gct att aca aat aca ttc aca aat cta aat tcg caa gaa agc gaa     384
Ala Ala Ile Thr Asn Thr Phe Thr Asn Leu Asn Ser Gln Glu Ser Glu
        115                 120                 125 gca tgg att ttt tat tac aaa gaa gat gca cat aaa act agt tac tat     432
Ala Trp Ile Phe Tyr Tyr Lys Glu Asp Ala His Lys Thr Ser Tyr Tyr
    130                 135                 140 tat aat atc tta ttt gct ata cag gat gag gaa aca ggt ggg gta atg     480
Tyr Asn Ile Leu Phe Ala Ile Gln Asp Glu Glu Thr Gly Gly Val Met
145                 150                 155                 160 gcg aca tta ccg att gca ttt gat att agt gta gat att gaa aaa gaa     528
Ala Thr Leu Pro Ile Ala Phe Asp Ile Ser Val Asp Ile Glu Lys Glu
                165                 170                 175 aag gtt cta ttt gtt act atc aag gat act gaa aat tat gcg gtt aca     576
Lys Val Leu Phe Val Thr Ile Lys Asp Thr Glu Asn Tyr Ala Val Thr
            180                 185                 190 gta aaa gct att aat gta gta caa gca ctt caa tct tcc cga gat tca     624
Val Lys Ala Ile Asn Val Val Gln Ala Leu Gln Ser Ser Arg Asp Ser
        195                 200                 205 aaa gtt gta gat gct ttt aaa tcg cca cgt cac tta cct aga aaa aga     672
Lys Val Val Asp Ala Phe Lys Ser Pro Arg His Leu Pro Arg Lys Arg
    210                 215                 220 cat aaa att tgt agt aac tct                                         693
His Lys Ile Cys Ser Asn Ser
225                 230
```

<210> SEQ ID NO 2
<211> LENGTH: 231
<212> TYPE: PRT
<213> ORGANISM: Bacillus thuringiensis

<400> SEQUENCE: 2

```
Met Phe Phe Asn Arg Val Ile Thr Leu Thr Val Pro Ser Ser Asp Val
1               5                   10                  15

Val Asn Tyr Ser Glu Ile Tyr Gln Val Ala Pro Gln Tyr Val Asn Gln
            20                  25                  30

Ala Leu Thr Leu Ala Lys Tyr Phe Gln Gly Ala Ile Asp Gly Ser Thr
        35                  40                  45

Leu Arg Phe Asp Phe Glu Lys Ala Leu Gln Ile Ala Asn Asp Ile Pro
    50                  55                  60

Gln Ala Ala Val Val Asn Thr Leu Asn Gln Thr Val Gln Gln Gly Thr
65                  70                  75                  80

Val Gln Val Ser Val Met Ile Asp Lys Ile Val Asp Ile Met Lys Asn
                85                  90                  95

Val Leu Ser Ile Val Ile Asp Asn Lys Lys Phe Trp Asp Gln Val Thr
            100                 105                 110

Ala Ala Ile Thr Asn Thr Phe Thr Asn Leu Asn Ser Gln Glu Ser Glu
        115                 120                 125

Ala Trp Ile Phe Tyr Tyr Lys Glu Asp Ala His Lys Thr Ser Tyr Tyr
    130                 135                 140

Tyr Asn Ile Leu Phe Ala Ile Gln Asp Glu Glu Thr Gly Gly Val Met
145                 150                 155                 160

Ala Thr Leu Pro Ile Ala Phe Asp Ile Ser Val Asp Ile Glu Lys Glu
                165                 170                 175

Lys Val Leu Phe Val Thr Ile Lys Asp Thr Glu Asn Tyr Ala Val Thr
            180                 185                 190

Val Lys Ala Ile Asn Val Val Gln Ala Leu Gln Ser Ser Arg Asp Ser
        195                 200                 205

Lys Val Val Asp Ala Phe Lys Ser Pro Arg His Leu Pro Arg Lys Arg
    210                 215                 220

His Lys Ile Cys Ser Asn Ser
225                 230
```

<210> SEQ ID NO 3
<211> LENGTH: 15
<212> TYPE: PRT
<213> ORGANISM: Bacillus thuringiensis

<400> SEQUENCE: 3

```
Met Phe Phe Asn Arg Val Ile Thr Leu Thr Val Pro Ser Ser Asp
1               5                   10                  15
```

<210> SEQ ID NO 4
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 4
atgtttttta atagagtaat tacattaaca gtac      34

BACILLUS THURINGIENSIS CRYET29 COMPOSITIONS TOXIC TO COLEOPTERAN INSECTS AND CTENOCEPHALIDES SPP

This application is a continuation of application Ser. No. 10/767,605, filed Jan. 29, 2004, now U.S. Pat. No. 7,186,893 which is a divisional of application Ser. No. 10/386,972, filed Mar. 12, 2003, now U.S. Pat. No. 6,686,452, which is a divisional of application Ser. No. 09/611,216 filed Jul. 6, 2000, now U.S. Pat. No. 6,537,756, which is a divisional of application Ser. No. 08/721,259, filed Sep. 26, 1996, now U.S. Pat. No. 6,093,695, the entire content of each is hereby specifically incorporated by reference.

1. BACKGROUND OF THE INVENTION

1.1 Field of the Invention

The present invention relates generally to the fields of molecular biology. More particularly, certain embodiments concern methods and compositions comprising DNA segments, and proteins derived from bacterial species. More particularly, it concerns a novel cryET29 gene from *Bacillus thuringiensis* encoding a coleopteran- and cat flea-toxic crystal protein. Various methods for making and using these DNA segments, DNA segments encoding synthetically-modified CryET29 proteins, and native and synthetic crystal proteins are disclosed, such as, for example, the use of DNA segments as diagnostic probes and templates for protein production, and the use of proteins, fusion protein carriers and peptides in various immunological and diagnostic applications. Also disclosed are methods of making and using nucleic acid segments in the development of transgenic plant cells containing the DNA segments disclosed herein.

1.2 Description of the Related Art

1.2.1 Bacillus thuringiensis Crystal Proteins

*Bacillus thuringiensis* is a Gram-positive bacterium that produces δ-endotoxins known as crystal proteins which are specifically toxic to certain orders and species of insects. Many different strains of *B. thuringiensis* have been shown to produce insecticidal crystal proteins. Compositions including *B. thuringiensis* strains which produce insecticidal proteins have been commercially available and used as environmentally acceptable insecticides because they are quite toxic to the specific target insect, but are harmless to plants and other non-targeted organisms.

The *B. thuringiensis* crystal protein is toxic in the insect only after ingestion when the alkaline pH and proteolytic enzymes in the insect mid-gut solubilize the crystal protein and release the toxic components. These components disrupt the mid-gut cells causing the insect to cease feeding and, eventually to die. In fact, *B. thuringiensis* has proven to be an effective and environmentally safe insecticide in dealing with various insect pests.

As noted by Hofte et al., (1989) the majority of insecticidal *B. thuringiensis* strains are active against insect of the order Lepidoptera, i.e., caterpillar insects. Other *B. thuringiensis* strains are insecticidally active against insects of the order Diptera, i.e., flies and mosquitoes, or against both lepidopteran and dipteran insects. In recent years, a few *B. thuringiensis* strains have been reported as producing crystal proteins that are toxic to insects of the order Coleoptera, i.e., beetles. To date, there have been no reports of *B. thuringiensis* strains active on fleas of the Genus, *Ctenocephalides*, in the order Siphonaptera.

The dipteran-active Cyt toxins differ from most of the other *B. thuringiensis* insecticidal crystal proteins in that they are smaller and do not share conserved blocks of sequence homology. These proteins demonstrate broad cytolytic activity in vitro, yet are specifically toxic to larvae of dipteran insects in vivo. These properties have been described elsewhere (Chilcott and Ellar, 1988).

1.2.2 Genetics of Crystal Proteins

A number of genes encoding crystal proteins have been cloned from several strains of *B. thuringiensis*. The review by Höfte et al. (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins. cryII genes encode CryII proteins that are toxic to both lepidopterans and dipterans. cryIII genes encode coleopteran-toxic CryIII proteins, while cryIV genes encode dipteran-toxic CryIV proteins.

Recently a new nomenclature has been proposed which systematically classifies the cry genes based upon DNA sequence homology rather than upon insect specificities. This classification scheme is shown in Table 1.

TABLE 1

Revised *B. thuringiensis* δ-Endotoxin Gene Nomenclature[a]

| New | Old | GenBank Accession # |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1G | PrtA | Z22510 |
| Cry1H | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry5B |  | U19725 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |

TABLE 1-continued

Revised *B. thuringiensis* δ-Endotoxin Gene Nomenclature[a]

| New | Old | GenBank Accession # |
|---|---|---|
| Cry11B | Jeg80 | X86902 |
| Cry12A | CryVB | L07027 |
| Cry13A | CryVC | L07023 |
| Cry14A | CryVD | U13955 |
| Cry15A | 34 kDa | M76442 |
| Cry16A | cbm71 | X94146 |
| Cyt1A | CytA | X03182 |
| Cyt2A | CytB | Z14147 |
| To Be Assigned | CryET29, Present Invention | To Be Assigned |

[a]Adapted from: Crickmore, N. et al. Microbiol. and Mol. Bio. Rev. (1998) Vol. 62: 807-813.

1.2.3 Identification of Crystal Proteins Toxic to Coleopteran Insects

The cloning and expression of a gene encoding a 26-kDa mosquitocidal toxin from the dipteran-active *B. thuringiensis* var. *israelensis* has been described (Ward et al., 1984), and the nucleotide sequence of this gene was reported (Ward and Ellar, 1986). The molecular mass of the toxin protein, CytA, calculated from the deduced amino acid sequence was determined to be 27,340 Da.

The nucleotide sequence of the gene for a 27-kDa mosquitocidal Cyt protein isolated from *B. thuringiensis* var. *morrisoni* strain PG14 has been disclosed (Earp and Ellar, 1987). The sequence of this toxin protein was found to differ by only one amino acid residue from the CytIA protein of *B. thuringiensis* var. *israelensis*.

The identification of a 25-kDa protein that exhibits cytolytic activity in vitro when activated by proteolysis from the mosquitocidal *B. thuringiensis* var. *kyushuensis* was described earlier (Knowles et al., 1992), and the nucleotide sequence of the gene for this protein, CytB, was reported (Koni and Ellar, 1993). The predicted molecular mass of the CytB protein is 29,236 Da and the deduced amino acid sequence is quite distinct, although it does share significant sequence similarity with the CytA protein of *B. thuringiensis* var. *israelensis*.

The cloning and characterization of the gene for a 30-kDa toxin protein with activity on coleopteran and dipteran insects has been described (Intl. Pat. Appl. Pub. No. WO 95/02693, 1995). This gene, isolated from *B. thuringiensis* PS201T6, encodes a protein of 29,906 Da which exhibits a 64% sequence identity with the CytA toxin of *B. thuringiensis* var. *israelensis*.

2. SUMMARY OF THE INVENTION

The present invention provides a novel *B. thuringiensis* insecticidal crystal protein (designated CryET29) and the gene which encodes it (designated cryET29) which contain amino acid and nucleic acid sequences, respectively, showing little homology to the δ-endotoxin proteins and genes of the prior art. Surprisingly, the CryET29 protein of the present invention demonstrates remarkable insecticidal activity against not only insects of the order Coleoptera, but also against fleas, and in particular larvae of the cat flea, *Ctenocephalides felis*.

In one important embodiment, the invention provides an isolated and purified amino acid segment comprising a *B. thuringiensis* CryET29 insecticidal crystal protein (SEQ ID NO:2) comprising the amino acid sequence illustrated in FIG. 1A and FIG. 1B. The coding region for the CryET29 protein is from nucleotide 29 to 721 of SEQ ID NO:1. The CryET29 protein exhibits insecticidal activity against Coleopterans such as the southern corn rootworm, western corn rootworm, Colorado potato beetle, Japanese beetle, and red flour beetle. In related embodiments, methods for making and using this protein, derivatives and mutants thereof, and antibodies directed against these proteins are also disclosed.

In another important embodiment, the invention provides an isolated and purified nucleic acid segment comprising the cryET29 gene which encodes the CryET29 crystal protein disclosed herein. The nucleotide sequence of the cryET29 gene is given in SEQ ID NO:1 and illustrated in FIG. 1A and FIG. 1B. In related embodiments, methods for making, using, altering, mutagenizing, assaying, and quantitating these nucleic acid segments are also disclosed. Also disclosed are diagnostic methods and assay kits for the identification and detection of related cry gene sequences in a variety of in vitro and in vivo methodologies.

Another aspect of the present invention is a *Bacillus thuringiensis* cell that produces a CryET29 crystal protein. In a preferred embodiment, the cell is a *Bacillus thuringiensis* bacterial strain designated *B. thuringiensis* EG4096 which has been deposited with the Agricultural Research Culture Collection, Northern Regional Research Laboratory (NRRL), on May 30, 1996 and assigned the Accession No. NRRL B-21582. *B. thuringiensis* EG4096, further described in Examples 1, 2, and 3, is a naturally-occurring bacterium that comprises a cryET29 gene (SEQ ID NO:1) of the present invention. EG4096 produces a novel insecticidal crystal protein of approximately 26-kDa, which the inventors have designated CryET29 (SEQ ID NO:2). Most preferably, the *Bacillus thuringiensis* cell has the NRRL accession number NRRL B-21582.

A further aspect of the present invention is a plasmid, cosmid, or vector that comprises the nucleic acid sequence of a whole or a portion of the cryET29 gene (SEQ NO ID:1), a transformed host cell comprising a native or recombinant cryET29 gene, a culture of a recombinant bacterium transformed with such plasmid, the bacterium preferably being *B. thuringiensis* such as the recombinant strains EG11494 and EG11502, described in Example 7, and most preferably a biologically-pure culture of such a bacterial strain. EG11494 was deposited on May 30, 1996 under the terms of the Budapest Treaty with the NRRL and given the Accession number NRRL B-21583. Alternatively, the *E. coli* recombinant strains EG11513 and EG1514 comprising the novel cryET29 gene, are also preferred hosts for expression of the CryET29 protein.

2.1 cryET29 DNA Segments

The present invention also concerns DNA segments, that can be isolated from virtually any source, that are free from total genomic DNA and that encode the whole or a portion of the novel peptides disclosed herein. The cryET29 gene (SEQ ID NO:1; FIG. 1A and FIG. 1B) encodes the 26-kDa CryET29 protein having an amino acid sequence shown in FIG. 1A and FIG. 1B (SEQ ID NO:2). DNA segments encoding these peptide species may prove to encode proteins, polypeptides, subunits, functional domains, and the like of crystal protein-related or other non related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a crystal protein or peptide refers to a DNA segment that contains crystal protein coding sequences yet is isolated away from, or purified free from, total genomic DNA of the species from which the DNA segment is obtained, which in the instant case is the genome of the Gram-positive bacterial genus, *Bacillus*, and in particular, the species known as *B. thuringiensis*. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified crystal protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extrachromosomal DNA sequences, but also operon sequences and/or engineered gene segments that express, or may be adapted to express, proteins, polypeptides or peptides.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a Cry protein or peptide species that includes within its amino acid sequence an amino acid sequence essentially as set forth in SEQ ID NO:2. More preferably, the DNA sequence comprises a nucleic acid sequence that encodes a Cry protein or peptide species that includes within its amino acid sequence an at least ten amino acid contiguous sequence of SEQ ID NO:2.

The term "a sequence essentially as set forth in SEQ ID NO:2," means that the sequence substantially corresponds to a portion of the sequence of SEQ ID NO:2 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:2 will be sequences that are "essentially as set forth in SEQ ID NO:2."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ ID NO:2, or that are identical to or complementary to DNA sequences which encode the peptide disclosed in SEQ ID NO:2, and particularly the DNA segment disclosed in SEQ ID NO:1. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; and up to and including sequences of about 10,000 nucleotides and the like.

It will also be understood that this invention is not limited to the particular nucleic acid sequences which encode peptides of the present invention, or which encode the amino acid sequence of SEQ ID NO:2, including the DNA sequence which is particularly disclosed in SEQ ID NO:1. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.2 DNA Segments as Hybridization Probes and Primers

In addition to their use in directing the expression of crystal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences) will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to the DNA sequence of SEQ ID NO:1, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1991, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 Recombinant Vectors and Protein Expression

The invention also discloses and claims a composition comprising a CryET29 crystal protein. The composition may comprises bacterial host cells which express a CryET29 crystal protein, inclusion bodies or crystals containing the CryET29 protein, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing crystal proteins are well-known to those of skill in the art of bacterial protein isolation and purification. In certain embodiments, the crystal proteins may be purified, concentrated, admixed with other reagents, or processed to a desired final form. Preferably, the composition will comprise from about 1% to about 90% by weight of the crystal protein, and more preferably from about 5%, to about 50% by weight.

In a preferred embodiment, the crystal protein compositions of the invention may be prepared by a process which comprises the steps of culturing a *Bacillus thuringiensis* cell which expresses a CryET29 crystal protein under conditions effective to produce such a protein, and then obtaining the protein from the cell. The obtaining of such a crystal protein may further include purifying, concentrating, processing, or admixing the protein with one or more reagents. Preferably, the CryET29 crystal protein is obtained in an amount of from between about 1% to about 90% by weight and more preferably from about 5% to about 50% by weight.

The invention also relates to a method of preparing a CryET29 crystal protein composition. Such a method generally involves the steps of culturing a *Bacillus thuringiensis* cell which expresses a CryET29 crystal protein under conditions effective to produce the protein, and then obtaining the protein so produced. In a preferred embodiment the *Bacillus thuringiensis* cell is an NRRL B-21582 cell, or any *Bacillus thuringiensis* cell which contains a cryET29 gene segment. Alternatively, the recombinant plasmid vectors of the invention may be used to transform other suitable bacterial or eukaryotic cells to produce the crystal protein of the invention. Prokaryotic host cells including Gram-negative cells such as *E. coli, Pseudomonas* spp. and related *Enterobacteraceae*, or Gram-positive cells such as *Bacillus* spp. (including *B. megaterium, B. subtilis*, and *B. thuringiensis*) and the like are all contemplated to be useful in the preparation of the crystal proteins of the invention. Particularly preferred *E. coli* strains include NRRL B-21624, deposited with the NRRL under the terms of the Budapest Treaty.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2.

2.4 Crystal Protein Transgenes and Transgenic Host Cells

In yet another aspect, the present invention provides methods for producing a transgenic cell, and in particular a plant or animal cell which expresses a nucleic acid segment encoding the novel CryET29 crystal protein of the present invention. The process of producing transgenic cells is well-known in the art. In general, the method comprises transforming a suitable host cell with a DNA segment which contains a promoter operatively linked to a coding region that encodes a *B. thuringiensis* CryET29 crystal protein. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

In a preferred embodiment, the invention encompasses a plant cell which has been transformed with a nucleic acid segment of the invention, and which expresses a gene or gene segment encoding one or more of the novel polypeptide compositions disclosed herein. As used herein, the term "transgenic plant cell" is intended to refer to a plant cell that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of a cryET29 transgene, either native cryET29, or synthetically modified or mutated cryET29. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant. In preferred embodiments, the introduction of the transgene into the genome of the plant cell results in a stable integration wherein the offspring of such plants also contain a copy of the transgene in their genome. The inheritibility of this genetic element by the progeny of the plant into which the gene was originally introduced is a preferred aspect of this invention.

A preferred gene which may be introduced includes, for example, a crystal protein-encoding a DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference), and are briefly discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding a CryET29 crystal protein which is toxic to coleopteran insects. Particularly preferred plants include corn, wheat, soybeans, turf grasses, ornamental plants, fruit trees, shrubs, vegetables, grains, legumes, and the like, or any plant into which introduction of a crystal protein transgene is desired.

In a related aspect, the present invention also encompasses a seed produced by the transformed plant, a progeny from such seed, and a seed produced by the progeny of the original transgenic plant, produced in accordance with the above process. Such progeny and seeds will have a crystal protein transgene stably incorporated into its genome, and such progeny plants will inherit the traits afforded by the introduction of a stable transgene in Mendelian fashion. All such transgenic plants having incorporated into their genome transgenic DNA segments encoding a CryET29 crystal protein or polypeptide are aspects of this invention.

2.5 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.6 Antibody Compositions and Methods of Producing

In particular embodiments, the inventors contemplate the use of antibodies, either monoclonal or polyclonal which bind to the crystal proteins disclosed herein. Means for preparing and characterizing antibodies are well known in the art (See, e.g, Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH)

and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified crystal protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60-61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, OF, NSO/U, MPC-11, MPC11-X45-GTG 1.7 and S 194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et aL, 1977). The use of electrically induced fusion methods is also appropriate (Goding, 1986, pp. 71-74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.7 Crystal Protein Screening and Immunodetection Kits

The present invention also provides compositions, methods and kits for screening samples suspected of containing a CryET29 δ-endotoxin or a gene encoding such a crystal protein. Such screening may be performed on samples such as transformed host cells, transgenic plants, progeny or seed thereof, or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a crystal protein or peptide or a crystal protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides. Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.8 ELISAs and Immunoprecipitation

ELISAs may be used in conjunction with the invention. In an ELISA assay, proteins or peptides incorporating crystal protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/TWEEN® surface active agent (ICI Americas, Inc., Wilmington, Del.). These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/TWEEN® surface active agent, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS/TWEEN®) surface active agent.

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-crystal protein antibodies of the present invention are particularly useful for the isolation of other crystal protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

2.9 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

2.10 Epitopic Core Sequences

The present invention is also directed to protein or peptide compositions, free from total cells and other peptides, which comprise a purified protein or peptide which incorporates an epitope that is immunologically cross-reactive with one or more anti-crystal protein antibodies. In particular, the invention concerns epitopic core sequences derived from Cry proteins or peptides.

As used herein, the term "incorporating an epitope(s) that is immunologically cross-reactive with one or more anti-crystal protein antibodies" is intended to refer to a peptide or protein antigen which includes a primary, secondary or tertiary structure similar to an epitope located within a crystal protein or polypeptide. The level of similarity will generally be to such a degree that monoclonal or polyclonal antibodies directed against the crystal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Cry immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic crystal protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to crystal proteins, and in particular Cry and Cry-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the crystal protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.11 Crystal Protein Compositions as Insecticides and Methods of Use

The inventors contemplate that the crystal protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel crystal protein disclosed herein. Preferably the cells are *B. thuringiensis* EG4096, EG 11494, or EG11502 cells, however, any such bacterial host cell expressing the novel nucleic acid segments disclosed herein and producing a crystal protein is contemplated to be useful, such as *B. megaterium, B. subtilis, E. coli*, or *Pseudomonas* spp.

In another important embodiment, the bioinsecticide composition comprises a water dispersible granule. This granule comprises bacterial cells which expresses a novel crystal protein disclosed herein. Preferred bacterial cells are *B. thuringiensis* EG4096, EG 11494, or EG11502 cells, however, bacteria such as *B. megaterium, B. subtilis, E. coli*, or *Pseudomonas* spp. cells transformed with a DNA segment disclosed herein and expressing the crystal protein are also contemplated to be useful.

In a third important embodiment, the bioinsecticide composition comprises a wettable powder, dust, pellet, or collodial concentrate. This powder comprises bacterial cells which expresses a novel crystal protein disclosed herein. Preferred bacterial cells are *B. thuringiensis* EG4096, EG11494, or EG11502 cells, however, bacteria such as *B. megaterium, B. subtilis, E. coli*, or *Pseudomonas* spp. cells transformed with a DNA segment disclosed herein and expressing the crystal protein are also contemplated to be useful. Such dry forms of the insecticidal compositions may be formulated to dissolve immediately upon wetting, or alternatively, dissolve in a controlled-release, sustained release, or other time-dependent manner.

In a fourth important embodiment, the bioinsecticide composition comprises an aqueous suspension of bacterial cells such as those described above which express the crystal protein. Such aqueous suspensions may be provided as a concentrated stock solution which is diluted prior to application, or alternatively, as a diluted solution ready-to-apply.

For these methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel CryET29 or CryET29-derived protein may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or collodial preparations of such crystals and/or spores as the active bioinsecticidal composition.

Regardless of the method of application, the amount of the active component(s) are applied at an insecticidally-effective amount, which will vary depending on such factors as, for example, the specific coleopteran insects to be controlled, the specific plant or crop to be treated, the environmental conditions, and the method, rate, and quantity of application of the insecticidally-active composition.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target coleopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations which comprise intact bacterial cells will generally contain from about $10^4$ to about $10^{12}$ cells/mg.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

2.12 Pharmaceutical Compositions and Methods for the Treatment of Fleas

Since the novel crystal protein of the present invention is the first such *B. thuringiensis* δ-endotoxin identified which has insecticidal activity against fleas, the inventors also contemplate the formulation of pharmaceutical compositions which may be given to animals as prophylaxis and/or treatment of infestation by fleas, and in particular by infestation of members of the Genus *Ctenocephalides*, such as *Ctenocephalides felis* (common name, cat flea) and *C. canis* (common name, dog flea). While these are only two members of the Order Siphonaptera for which the present invention's compositions demonstrate insecticidal activity, it is contemplated that the compositions may be useful in treating other related insects which commonly attack animals may also be controlled by the novel compositions disclosed herein. Such insects are described in detail in U.S. Pat. No. 5,449,681, incorporated herein by reference, and include members of the Genera *Culex, Culiseta, Bovicola, Callitroga, Chrysops, Cimes, Ctenocephalis, Dermatophilus, Dermatobia*, and *Damalinia* among others.

As such, one aspect of the invention comprises a pharmaceutical composition comprising a crystal protein composition disclosed herein for administration to an animal to prevent or reduce flea or related insect infestation. A method of reducing such flea infestation in an animal is also disclosed and claimed herein. The method generally comprises administering to an animal an insecticidally-effective amount of a CryET29 composition. Means for administering such insecticidal compositions to an animal are well-known in the art. U.S. Pat. No. 5,416,102 (specifically incorporated herein by reference) provides teaching for methods and formulations for preventing flea infestation using an insecticidal composition.

Such anti-siphonapteran veterinary compositions may be delivered in a variety of methods depending upon the particular application. Examples of means for administering insecticidal compositions to an animal are well-known to those of skill in the art, and include, e.g., flea collars, flea sprays, dips, powders and the like. Methods for providing such formulations to an animal are also well-known to those of skill in the art, and include direct application or passive application such as the device described in U.S. Pat. No. 4,008,688 for the application of insecticides by a pet bed assembly. The animal to be treated may be any animal which is sensitive to or susceptible to attack or infestation by a flea which is killed or inhibited by a CryET29 composition as disclosed herein. Such animals may be feline, canine, equine, porcine, lupine, bovine, murine, etc. and the like, although the inventors contemplate that feline and canine animals will be particularly preferred as animals to be treated by the novel compositions disclosed herein.

It is further contemplated that in addition to topical administration of the pharmaceutical compositions disclosed, systemic administration may in some cases be preferable or desirable. For oral administration, the compositions may be formulated with an inert diluent or with an assimilable edible carrier, or they may be enclosed in hard- or soft-shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

For oral prophylaxis of fleas, the crystal protein may be incorporated with excipients and used in the form of a gel, paste, powder, pill, tablet, capsule, or slurry which may be given to the animal for ingestion. Alternatively the compositions may be formulated as an additive to pet foods, treats, or other edible formulations. When formulated as a tablet or capsule, or the like, the composition may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent to make the composition more palatable to the animal being treated. One such means for delivering flea prophylactics to an animal is a sauce as described in U.S. Pat. No. 4,702,914, specifically incorporated herein by reference.

When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. Of course, any material used in preparing any dosage unit form should be pharmaceutically pure and substantially non-toxic in the amounts employed. In addition, the active compounds may be incorporated into sustained-release preparation and formulations.

Alternatively, the pharmaceutical compositions disclosed herein may be administered parenterally, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

When systemic administration is desired, e.g., parenteral administration in an aqueous solution, the solution should be suitably buffered if necessary and the liquid diluent first rendered isotonic with sufficient saline or glucose. These particular aqueous solutions are especially suitable for intramuscular, subcutaneous and intraperitoneal administration. In this connection, sterile aqueous media which can be employed will be known to those of skill in the art in light of the present disclosure. Some variation in dosage will necessarily occur depending on the condition, size, and type of animal being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as creams, lotions, sprays, dips, emulsions, colloids, or alternatively, when systemic administration is desirable, injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a animal. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Another aspect of the invention encompasses methods and compositions for use in the control and eradication of siphonapteran insects from environmental areas where infestation by such insects is suspected. The method generally involves applying to an area suspected of containing such insects an insecticidally-effective amount of a CryET29 composition as disclosed herein. The inventors further contemplate the use of the protein of the present invention as an active ingredient in a pharmaceutical composition for administration to body or to the living areas and environs of an animal to prevent, lessen, or reduce the infestation of fleas and related insects in such areas. The crystal protein composition may be formulated in a powder, spray, fog, granule, rinse, shampoo, flea collar, dip, etc. suitable for administration to the body of the animal or to the living quarters, bedding materials, houses, yards, kennels, pet boarding facilities etc. of such an animal using techniques which are known to those of skill in the art of veterinary insecticide formulations. An example of oral formulation of veterinary insecticides is found in the teachings of U.S. Pat. No. 5,416,102. The inventors contemplate that the use of such compositions in the prevention or eradication of fleas on pets such as dogs, cats, and other fur-bearing animals may represent a significant advance in the state of the art considering the novel compositions disclosed herein are the first crystal proteins identified which have such desirable anti-siphonapteran insecticidal activity.

2.13 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 2.

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Giutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

3. BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B show the nucleic acid sequence of the cryET29 gene (SEQ ID NO:1), and the corresponding deduced amino acid sequence of the CryET29 protein (SEQ ID NO:2).

4. DESCRIPTION OF ILLUSTRATIVE EMBODIMENTS

The present invention provides a novel δ-endotoxin, designated CryET29, which is toxic to larvae of the cat flea, *Ctenocephalides felis*, as well as against coleopteran insects such as the southern and western corn rootworm, Colorado potato beetle, Japanese beetle, and the red flour beetle. It is important to note that the trivial name for *Ctenocephalides felis* is somewhat misleading in that the organism parasitizes not only felines, but is the major parasitic flea for canines as well (see e.g., U.S. Pat. No. 4,547,360, specifically incorporated herein by reference).

4.1 cryET29 DNA Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein gene sequence, e.g., a sequence such as that shown in SEQ ID NO:1. The ability of such nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCR™ using such primers.

4.2 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus* crystal proteins include any of the known crystal protein gene promoters, including the cryET29 gene promoter, and promoters specific for *B. thuringiensis* sigma factors, such as $\sigma^E$ and $\sigma^K$ (for a review see Baum and Malvar, 1995) Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP Carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a CryET29 *B. thuringiensis* crystal protein-encoding gene. In preferred embodiments, such a polypeptide has the amino acid residue sequence of SEQ ID NO:2, or a functional equivalent of this sequence. In accordance with such embodiments, a coding region comprising the DNA sequence of SEQ ID NO:1 is also preferred.

4.3 Characteristics of the CryET29 Crystal Protein

The present invention provides novel polypeptides that define a whole or a portion of a *B. thuringiensis* CryET29 crystal protein.

In a preferred embodiment, the invention discloses and claims an isolated and purified CryET29 protein. The CryET29 protein comprises an amino acid sequence as disclosed in SEQ ID NO:2. CryET29 has a calculated isoelectric constant (pI) equal to 5.88. The amino acid composition of the CryET29 protein is given in Table 3.

TABLE 3

Amino Acid Composition of CryET29

| Amino Acid | # Residues | % Total |
|---|---|---|
| Ala | 18 | 7.7 |
| Arg | 7 | 3.0 |
| Asn | 15 | 6.4 |
| Asp | 15 | 6.4 |
| Cys | 1 | 0.4 |
| Gln | 15 | 6.4 |
| Glu | 10 | 4.3 |
| Gly | 5 | 2.1 |
| His | 3 | 1.2 |
| Ile | 20 | 8.6 |
| Leu | 13 | 5.6 |
| Lys | 16 | 6.9 |
| Met | 4 | 1.7 |
| Phe | 12 | 5.1 |
| Pro | 6 | 2.5 |
| Ser | 16 | 6.9 |
| Thr | 17 | 7.3 |
| Trp | 2 | 0.8 |
| Tyr | 10 | 4.3 |
| Val | 26 | 11.2 |
| Acidic (Asp + Glu) | 25 | 10.7 |
| Basic (Arg + Lys) | 23 | 9.9 |
| Aromatic (Phe + Trp + Tyr) | 24 | 10.2 |
| Hydrophobic (Aromatic + Ile + Leu + Met + Val) | 87 | 37.3 |

4.4 Transformed or Transgenic Plant Cells

A bacterium, a yeast cell, or a plant cell or a plant transformed with an expression vector of the present invention is also contemplated. A transgenic bacterium, yeast cell, plant cell or plant derived from such a transformed or transgenic cell is also contemplated. Means for transforming bacteria and yeast cells are well known in the art. Typically, means of transformation are similar to those well known means used to transform other bacteria or yeast such as *E. coli* or *Saccharomyces cerevisiae.*

Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

4.5.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.5.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into a monocot cell by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.5.3 *Agrobacterium*-Mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for *Agrobacterium*, although transgenic plants have been produced in asparagus using *Agrobacterium* vectors as described (Bytebier et al., 1987). Therefore, commercially important cereal grains such as rice, corn, and wheat must usually be transformed using alternative methods. However, as mentioned above, the transformation of asparagus using *Agrobacterium* can also be achieved (see, for example, Bytebier et al., 1987).

A transgenic plant formed using *Agrobacterium* transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced insecticidal activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and outcrossing with a non-transgenic plant are also contemplated.

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.6 Methods for Producing Insect-Resistant Transgenic Plants

By transforming a suitable host cell, such as a plant cell, with a recombinant cryET29 gene-containing segment, the expression of the encoded crystal protein (i.e., a bacterial crystal protein or polypeptide having insecticidal activity against coleopterans) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before.

Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a cry gene) that encodes the Cry polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects and cat flea larvae, preferably in the field, under a range of environmental conditions. The inventors contemplate that the present invention will find particular utility in the creation of transgenic plants of commercial interest including various turf grasses, wheat, corn, rice, barley, oats, a variety of ornamental plants and vegetables, as well as a number of nut- and fruit-bearing trees and plants.

4.7 Nomenclature of the Novel Proteins

The inventors have arbitrarily assigned the designation CryET29 to the novel protein of the invention. Likewise, the arbitrary designation of cryET29 has been assigned to the novel nucleic acid sequence which encodes this polypeptide. Formal assignment of the gene and protein designations based on the revised nomenclature of crystal protein endotoxins (Table 1) will be assigned by a committee on the nomenclature of *B. thuringiensis*, formed to systematically classify *B. thuringiensis* crystal proteins. The inventors contemplate that the arbitrarily assigned designations of the present invention will be superseded by the official nomenclature assigned to these sequences.

4.8 Definitions

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation of *B. thuringiensis* EG4096

Crop dust samples were obtained from various sources throughout the U.S. and abroad, typically grain storage facilities. The crop dust samples were treated and spread on agar plates to isolate individual *Bacillus*-type colonies as described (Donovan et al., 1993). EG4096 is a wild-type *B. thuringiensis* strain isolated from a crop dust sample from Thailand. Phase contrast microscopy was used to visually examine the crystal morphology of the bacterial colonies from this crop dust. The colony designated EG4096 contained endospores and crystalline inclusions of a unique morphology resembling short needles. The array of plasmids native to strain EG4096 is also unique.

Insect bioassay of this wild-type *B. thuringiensis* strain determined that it had insecticidal activity against larvae of coleopteran insects, including Southern corn rootworm, western corn rootworm, Colorado potato beetle, red flour beetle, and Japanese beetle. EG4096 also exhibits insecticidal activity against larva of the cat flea.

Characterization of EG4096 included the analysis of crystal protein produced by the strain during sporulation and the cloning and expression of the gene encoding the crystal protein, which has been designated cryET29. The insecticidal activity of both the wild-type strain and of a recombinant *B. thuringiensis* expressing the cloned cryET29 toxin gene was determined.

5.2 Example 2

Evaluation of the Native Plasmids of *B. thuringiensis* Strain EG4096

The complement of native plasmids contained within isolated *B. thuringiensis* EG4096 was determined by modified Eckhardt agarose gel electrophoresis as described by Gonzalez et al., (1982). The pattern of native plasmids did not correspond to patterns of typical known serovars (Carlton and Gonzalez, 1985). The plasmid sizes are 5.0, 7.2, 6.0 (open circular), 39, 80 and 100 MDa.

5.3 Example 3

Evaluation of the Crystal Protein of *B. thuringiensis* EG4096

EG4096 was grown in DSM+ glucose sporulation medium [0.8% (wt/vol) Difco nutrient broth, 0.5% (wt/vol) glucose, 10 mM $K_2HPO_4$, 10 mM $KH_2PO_4$, 1 mM $Ca(NO_3)_2$, 0.5 mM $MgSO_4$, 10 μM $MnCl_2$, 10 μM $FeSO_4$] for three days at 30° C. during which the culture grew to stationary phase, sporulated and lysed, thus releasing the protein inclusions into the medium. The cultures were harvested by centrifugation which pelleted the spores and crystals. The pellet was washed in a solution of 0.005% Triton X-100®, 2 mM EDTA and recentrifuged. The washed pellet was resuspended at one-tenth the original volume of 0.005% Triton X-100®, 2 mM EDTA.

Crystal protein was solubilized from the spores-crystals suspension by incubating the suspension in solubilization buffer [0.14 M Tris-HCl pH 8.0, 2% (wt/vol) sodium dodecyl sulfate (SDS), 5% (vol/vol) 2-mercaptoethanol, 10% (vol/vol) glycerol, and 0.1% bromphenol blue] at 100° C. for 5 min. The solubilized crystal protein was size fractionated by SDS-PAGE. After size fractionation the proteins were visualized by Coomassie Brilliant Blue R-250 staining. This analysis showed that the major crystal protein present in sporulated cultures of EG4096 is approximately 25-kDa in size. This novel protein was designated CryET29.

To further characterize CryET29, the $NH_2$-terminal amino acid sequence of the protein was determined. A sporulated culture of EG4096 was washed and resuspended. The suspension was solubilized and run on an acrylamide gel following the procedures for SDS-PAGE analysis. After electrophoresis the proteins were transferred to a BioRad PVDF membrane following standard western blotting procedures. After transfer, the membrane was rinsed 3− in $dH_2O$ and washed in Amido Black 1013 stain for 1 min (Sigma Chemical Co., St. Louis, Mo.). The filter was destained 1 min in 5% acetic acid and then rinsed in 3 changes of $dH_2O$. The portion of the filter containing the approximately 25-kDa protein band was excised with a razor blade. This procedure resulted in a pure form of CryET29 being obtained as a protein blotted onto a PVDF membrane (BioRad, Hercules, Calif.).

The determination of the $NH_2$-terminal amino acid sequence of the purified CryET29 protein immobilized on the membrane was performed in the Department of Physiology at the Tufts Medical School, Boston, Mass. using standard automated Edman degradation procedures The $NH_2$-terminal sequence was determined to be:

```
                                        (SEQ ID NO:3)
1  2  3  4  5  6  7  8  9  10 11 12 13 14 15
MetPhePheAsnArgValIleThrLeuThrValProSerSerAsp
```

Computer algorithms (Korn and Queen, 1984) were used to compare the N-terminal sequence of the CryET29 protein with amino acid sequences of all *B. thuringiensis* crystal proteins of which the inventors are aware including the sequences of all *B. thuringiensis* crystal proteins which have been published in scientific literature, international patent applications, or issued patents. A list of the crystal proteins whose sequences have been published along with the source of publication is shown in Table 4.

TABLE 4

*B. thuringiensis* Crystal Proteins Described in the Literature

| Crystal Protein | Source or Reference |
|---|---|
| Cry1A(a) | J. Biol. Chem., 260: 6264-6272 |
| Cry1A(b) | DNA, 5: 305-314 |
| Cry1A(c) | Gene, 36: 289-300 |
| Cry1B | Nucl. Acids Res., 16: 4168-4169 |
| Cry1C | Nucl. Acids Res., 16: 6240 |
| Cry1Cb | Appl. Environ. Micro., 59: 1131-1137 |
| Cry1C(b) | Nucl. Acids Res., 18: 7443 |
| Cry1D | Nucl. Acids Res., 18: 5545 |
| Cry1E | EPO 358 557 A2 |
| Cry1F | J. Bacteriol., 173: 3966-3976 |
| Cry1G | FEBS, 293: 25-28 |
| CryV | WO 90/13651 |
| Cry2A | J. Biol. Chem., 263: 561-567 |
| Cry2B | J. Bacteriol., 171: 965-974 |
| Cry2C | FEMS Microbiol. Lett., 81: 31-36 |
| Cry3A | Proc. Natl. Acad. Sci. USA, 84: 7036-7040 |
| Cry3B | Nucl. Acids Res., 18: 1305 |
| Cry3B2 | Appl. Environ. Microbiol., 58: 3921-3927 |
| Cry3B3 | U.S. Pat. No.5,378,625 |
| Cry3C | Appl. Environ. Microbiol., 58: 2536-2542 |
| Cry3D | Gene, 110: 131-132 |
| Cry4A | Nucl. Acids Res., 15: 7195 |
| Cry4B | EPO 308,199 |
| Cry4C | J. Bacteriol., 166: 801-811 |
| Cry4D | J. Bacteriol., 170: 4732, 1988 |
| Cry5 | Molec. Micro., 6: 1211-1217 |
| Cry33AkD | WO 94/13785 |
| Cry33BkD | WO 94/13785 |
| Cry34kD | J. Bacteriol., 174: 549-557 |
| Cry40kD | J. Bacteriol., 174: 549-557 |
| Cry201T635 | WO 95/02693 |
| Cry517 | J. Gen. Micro., 138: 55-62 |
| Crya7A021 | EPO 256,553 B1 |
| CryAB78ORF1 | WO 94/21795 |
| CryAB780RF2 | WO 94/21795 |
| CryAB78100kD | WO 94/21795 |
| Crybtpgs1208 | EPO 382 990 |
| Crybtpgs 1245 | EPO 382 990 |
| Crybts02618A | WO 94/05771 |
| CryBuibui | WO 93/03154 |
| CryET4 | U.S. Pat. No.5,322,687 |
| CryET5 | U.S. Pat. No.5,322,687 |
| CryGei87 | EPO 238,441 |
| CryHD511 | U.S. Pat. No.5,286,486 |
| CryHD867 | U.S. Pat. No.6,286,486 |
| CryIPL | U.S. Pat. No.5,231,008 |
| CryMITS | JP 6000084 |
| CryPS17A | WO 92/19739 |
| CryPS17B | U.S. Pat. No.5,350,576 and 5,424,410 |
| CryP16 | WO 95/00639 |
| CryP18 | WO 95/00639 |
| CryP66 | WO 95/00639 |
| CryPS33F2 | WO 92/19739 and U.S. Pat. No.5,424,410 |
| CryPS40D1 | U.S. Pat. No.5,273,746 |
| CryPS43F | WO 93/04587 |
| CryPS 50Ca | WO 93/04587 and EPO 498,537 A2 |
| CryPS 50Cb | WO 93/15206 |
| Cryps52A1 | U.S. Pat. No.4,849,217 |
| CryPS63B | WO 92/19739 |
| CryPS69D1 | U.S. Pat. No.5,424,410 |
| Cryps71M3 | WO 95/02694 |
| CryPS80JJ1 | WO 94/16079 |
| CryPS81IA | U.S. Pat. No.5,273,746 |

TABLE 4-continued

B. thuringiensis Crystal Proteins Described in the Literature

| Crystal Protein | Source or Reference |
|---|---|
| CryPS81IA2 | EPO 405 810 |
| Cryps81A2 | EPO 401 979 |
| CryPS81IB | WO 93/14641 |
| CryPS81IB2 | U.S. Pat. No.5,273,746 |
| Cryps81f | U.S. Pat. No.5,045,469 |
| Cryps81gg | U.S. Pat. No.5,273,746 |
| Cryps81rrl | EPO 401 979 |
| Cryps86A1 | U.S. Pat. No.5,468,636 |
| CryX | FEBS Lett., 336: 79-82 |
| CryXenA24 | WO 95/00647 |
| CrycytA | Nucl. Acids Res., 13: 8207-8217 |

The N-terminal sequence of the CryET29 protein was not found to be homologous to any of the known *B. thuringiensis* crystal proteins identified in Table 4.

5.4 Example 4

Isolation of a DNA Fragment Comprising the *B. thuringiensis* EG4096 cryET29 Gene In order to identify the gene encoding the CryET29 protein, an oligonucleotide probe specific for the $NH_2$-terminal amino acid sequence of the protein was designed. Using codons typically found in *B. thuringiensis* toxin genes, an oligo of 35 nucleotides was synthesized by Integrated DNA Technologies, Inc. (Coralville, Iowa) and designated wd270. The sequence of wd270 is:

```
                                            (SEQ ID NO:4)
5'-ATGTTTTTTAATAGAGTAATTACATTAACAGTACC-3'
```

Radioactively-labeled wd270 was used as a probe in Southern blot studies as described below to identify a DNA restriction fragment containing the cryET29 gene. Total DNA was extracted from EG4096 by the following procedure. Vegetative cells were resuspended in a lysis buffer containing 50 mM glucose, 25 mM Tris-HCl (pH 8.0), 10 mM EDTA, and 4 mg/ml lysozyme. The suspension was incubated at 37° C. for one hr. Following incubation, the suspension was extracted with an equal volume of phenol, one time with an equal volume of phenol:chloroform:isoamyl alcohol (50:48:2), and once with an equal volume of chloroform:isoamyl alcohol (24:1). DNA was precipitated from the aqueous phase by the addition of one-tenth volume 3 M sodium acetate then two volumes of 100% ethanol. The precipitated DNA was collected by centrifugation, washed with 70% ethanol and resuspended in $dH_2O$.

The extracted DNA was then digested, in separate reactions, with various restriction endonucleases, including EcoRI. The digested DNA was size fractionated by electrophoresis through an 0.8% agarose gel in 1×TBE overnight at 2 V/cm. The fractionated DNA fragments were transferred to an Immobilon-NC nitrocellulose filter (Millipore Corp., Bedford, Mass.) according to the method of Southern (1975). DNA was fixed to the filter by baking at 80° C. in a vacuum oven.

To identify the DNA fragment(s) containing the sequence encoding the $NH_2$-terminus of the CryET29 protein (see Example 3) the oligonucleotide wd270 was radioactively labeled at the 5' ends and used as a hybridization probe. To radioactively label the probe, 1 to 5 pmoles wd270 was added to a reaction containing [$\gamma$-$^{32}$P] ATP (3 μl of 3,000 Ci/mmole at 10 mCi/ml in a 20 μl reaction volume), a 10× reaction buffer (700 mM Tris-HCl, pH 7.8, 100 mM $MgCl_2$, 50 mM DTT), and 10 units T4 polynucleotide kinase (Promega Corporation, Madison, Wis.). The reaction was incubated 20 minutes at 37° C. to allow the transfer of the radioactive phosphate to the 5' end of the oligonucleotide, thus making it useful as a hybridization probe.

The labeled probe was then incubated with the nitrocellulose filter overnight at 45° C. in 3×SSC, 0.1% SDS, 10×Denhardt's reagent (0.2% BSA, 0.2% polyvinylpyrrolidone, 0.2% ficoll), 0.2 mg/ml heparin. Following incubation the filter was washed in several changes of 3×SSC, 0.1% SDS at 45° C. The filter was blotted dry and exposed to Kodak X-OMAT AR X-ray film (Eastman Kodak Company, Rochester, N.Y.) overnight at −70° C. with a DuPont Cronex Lightning Plus screen.

The labeled probe was then incubated with the nitrocellulose filter which was then washed and exposed to X-ray film to obtain an autoradiogram.

Examination of the autoradiogram identified two distinct EcoRI restriction fragments, of approximately 5.0 kb and 7.0 kb, that specifically hybridized to the labeled wd270 probe. This result indicated that strain EG4096 either contained two closely related, or identical, copies of the cryET29 gene, both of which hybridize to the wd270 oligonucleotide.

5.5 Example 5

Cloning of the cryET29 Gene of *B. thuringiensis* EG4096

To isolate the 5.0 and 7.0 kilobase (kb) EcoRI restriction fragments containing the cryET29 gene, total genomic DNA was isolated from strain EG4096 as described in Example 4. The DNA was digested with EcoRI and electrophoresed through a 0.8% agarose, 1×TBE gel, overnight at 2 V/cm of gel length. The gel was stained with Ethidium bromide so that the digested DNA could be visualized when exposed to long-wave UV light. Gel slices containing DNA fragments of approximately 5.0 and 7.0 kb were excised from the gel with a razor blade and placed in separate dialysis bags containing a small volume (1 ml) of 10 mM Tris-HCl, pH 8.0, 1 mM EDTA (TE). The DNA fragments were eluted from the gel slices into the TE buffer by placing the dialysis bags in a horizontal electrophoresis apparatus filled with 1×TBE and applying 100 V for 2 hr. This results in the DNA fragments migrating out of the gel slice into the TE buffer. The TE buffer containing the eluted fragments was then phenol:chloroform extracted and ethanol precipitated.

To create a library in *E. coli* of the two sets of size selected EcoRI restriction fragments (approximately 5.0 and 7.0 kb), the fragments were ligated into the cloning vector pUC18 (Yanisch-Perron, et al., 1985). The plasmid DNA vector pUC18 can replicate at a high copy number in *E. coli* and carries the gene for resistance to the antibiotic ampicillin, which may be used as a selectable marker. The two sets of fragments were mixed, in separate reactions, with EcoRI-digested pUC18 that had been treated with bacterial alkaline phosphatase (GibcoBRL, Gaithersburg, Md.) to remove the 5' phosphates from the digested plasmid to prevent re-ligation of the vector to itself. T4 ligase and a ligation buffer (Promega Corporation, Madison, Wis.) were added to the reaction containing the digested pUC18 and the size-selected EcoRI fragments. These were incubated at room temperature for 1 hour to allow the insertion and ligation of the EcoRI fragments into the pUC18 vector DNA.

The ligation mixtures described above were introduced, separately, into transformation-competent *E. coli* DH5α™ cells (purchased from GibcoBRL, Gaithersburg, Md.) following procedures described by the manufacturer. The transformed *E. coli* cells were plated on LB agar plates containing 50 μg/ml ampicillin and incubated overnight at 37° C. Both transformations yielded approximately 300 ampicillin-resistant colonies indicating the presence of a recombinant plasmid in the cells of each colony.

To isolate the colonies harboring the cloned 5.0 and 7.0 kb EcoRI fragments that contain the cryET29 gene sequences the transformed *E. coli* colonies were first transferred to nitrocellulose filters. This was accomplished by simply placing a circular filter (Millipore HATF 085 25, Millipore Corp., Bedford, Mass.) directly on top of the LB-ampicillin agar plates containing the transformed colonies. When the filter is slowly peeled off of the plate the colonies stick to the filter giving an exact replica of the pattern of colonies from the original plate. Enough cells from each colony are left on the plate that 5 to 6 hr of growth at 37° C. will restore the colonies. The plates are then stored at 4° C. until needed. The nitrocellulose filters with the transferred colonies were then placed, colony-side up, on fresh LB-ampicillin agar plates and allowed to grow at 37° C. until they reached a size of approximately 1 mm in diameter.

To release the DNA from the recombinant *E. coli* cells onto the nitrocellulose filter the filters were placed, colony-side up, on 2 sheets of Whatman 3 MM Chr paper (Whatman International LTD., Maidstone, England) soaked with 0.5 N NaOH, 1.5 M NaCl for 15 min. This treatment lyses the cells and denatures the released DNA allowing it to stick to the nitrocellulose filter. The filters were then neutralized by placing the filters, colony-side up, on 2 sheets of Whatman paper soaked with 1 M $NH_4$-acetate, 0.02 M NaOH for 10 min. The filters were then rinsed in 3×SSC, air dried, and baked for 1 hr at 80° C. in a vacuum oven to prepare them for hybridization.

The $NH_2$-terminal oligonucleotide specific for the cryET29 gene, wd270, was labeled at the 5' end with $\gamma$-$^{32}$P and T4 polynucleotide kinase as described above. The labeled probe was added to the filters in 3×SSC, 0.1% SDS, 10×Denhardt's reagent (0.2% BSA, 0.2% polyvinylpyrrolidone, 0.2% ficoll), 0.2 mg/ml heparin and incubated overnight at 45° C. These conditions were chosen to allow hybridization of the labeled oligonucleotide to related sequences present on the nitrocellulose blots of the transformed *E. coli* colonies. Following incubation the filters were washed in several changes of 3×SSC, 0.1% SDS at 45° C. The filters were blotted dry and exposed to Kodak X-OMAT AR x-ray film (Eastman Kodak Company, Rochester, N.Y.) overnight at −70° C. with a DuPont Cronex Lightning Plus screen.

Several colonies from each transformation (the 5.0 and 7.0 kb ligation mixes described above) hybridized to wd270. These colonies were identified by lining up the signals on the autoradiogram with the colonies on the original transformation plates. The isolated colonies were then grown in LB-ampicillin liquid medium from which the cells could be harvested and recombinant plasmid prepared by the standard alkaline-lysis miniprep procedure (described in Maniatis et al., 1982). The isolated plasmids were digested with the restriction enzyme EcoRI to determine if the cloned fragments of EG4096 DNA were of the expected size. All of the hybridizing plasmids from both the 5.0 kb and 7.0 kb constructions had the expected size insert fragment. The DNA from these plasmid digests were electrophoresed through an agarose gel and transferred to nitrocellulose as described above. The blot was then hybridized with the oligonucleotide, wd270, that had been radioactively labeled at the 5' end with $\gamma$32P and T4 polynucleotide kinase. EcoRI fragments from two of the five plasmids containing 5.0 kb inserts hybridized to the probe confirming the presence of the cryET29 gene on those fragments. One of the plasmids with the 5.0 insert containing the cryET29 gene was designated pEG1298. EcoRI fragments from five of the six plasmids containing 7.0 kb inserts hybridized to the probe confirming the presence of the cryET29 gene on those fragments. One of the plasmids with the 7.0 kb insert containing the cryET29 gene was designated pEG1299, The *E. coli* strain containing pEG1298 has been designated EG11513. EG11513 has been deposited with the Agricultural Research Culture Collection, Northern Regional Research Laboratory (NRRL) having Accession No. NRRL B-21624. The *E. coli* strain containing pEG1299 has been designated EG11514.

5.6 Example 6

Determination of the DNA Sequence of the cryET29 Gene

A partial DNA sequence of the genes cloned on pEG1298 and pEG1299 was determined following established dideoxy chain-termination DNA sequencing procedures (Sanger et al., 1977). Preparation of the double stranded plasmid template DNA was accomplished using a Qiagen Plasmid Kit (Qiagen Inc., Chatsworth, Calif.) following manufacturer's procedures. The sequencing reactions were performed using the Sequenase™ Version 2.0 DNA Sequencing Kit (United States Biochemical/Amersham Life Science Inc., Cleveland, Ohio) following manufacturer's procedures and using $^{35}$S-dATP as the labeling isotope (obtained from Du Pont NEN® Research Products, Boston, Mass.). Denaturing gel electrophoresis of the reactions was done on a 6% (w/v) acrylamide, 42% (w/v) urea sequencing gel. The dried gel was exposed to Kodak X-OMAT AR X-ray film (Eastman Kodak Company, Rochester, N.Y.) overnight at room temperature.

The $NH_2$-terminal specific oligonucleotide wd270 was used as the initial sequencing primer. The partial DNA sequences indicated that the plasmids pEG1298 and pEG1299 contained either identical, or nearly identical, copies of the cryET29 gene of *B. thuringiensis* strain EG4096. The entire DNA sequence for the copies of cryET29 on the two plasmids was completed using the procedures described above. Successive oligonucleotides to be used for priming sequencing reactions were designed from the sequencing data of the previous set of reactions. In this way the DNA sequencing progressed along both the top and bottom strand of the cryET29 gene in a step-wise fashion.

The DNA sequence of both copies of the cryET29 (SEQ ID NO:1) gene is identical and is shown in FIG. 1. The protein coding portion of the cryET29 gene is comprised of 696 nucleotides, including a stop codon. The CryET29 protein (SEQ ID NO:2), as deduced from the DNA sequence, consists of 231 amino acids with a predicted molecular mass of 26,194 daltons.

Database searches were then conducted to determine if the deduced amino acid sequence of the CryET29 protein shares identity with other characterized proteins, especially other insecticidal toxin proteins. Database searches using on-line servers were performed with the BLASTP program (Altschul et al., 1990) provided by the National Center for Biotechnology Information (Bethesda, Md.). The BLASTP searches were run with the BLOSUM62 matrix. The searched database consisted of non-redundant GenBank CDS translations+PDB+SwissProt+SPupdate+PIR.

Only four proteins in these databases were identified with any significant identity to CryET29. These included the dipteran toxin CytB (55% identity; Koni and Ellar, 1993); the coleopteran/dipteran toxin CytA (44.2% identity; Ward et al., 1984); the dipteran toxin PS201T6 (41.1% identity; Intl. Pat. Appl. Publ. No. WO 95/02693) and the 27-kDa *Bacillus thuringiensis morrissoni* dipteran toxin (44.2% identity; Earp and Ellar, 1987).

5.7 Example 7

Expression of the Cloned cryET29 Gene

To characterize the properties of the CryET29 protein it was necessary to express the cloned cryET29 gene in *B. thuringiensis* cells that are negative for crystal proteins (Cry⁻). The cloned EcoRI fragments on pEG1298 and pEG1299 was inserted into a plasmid vector capable of replicating in *B. thuringiensis*, thus allowing the expression of cloned genes.

pEG1298 and pEG1299 were digested with EcoRI to remove the cloned 5 kb and 7 kb fragments, respectively. The digested plasmids were resolved on an agarose gel and the desired fragments were purified from gel slices using the GeneClean® procedure of Bio101, Inc. (Vista, Calif.). The fragments were ligated, separately, into a *B. thuringiensis/E. coli* shuttle vector that had been digested with EcoRI and treated with bacterial alkaline phosphatase. The shuttle vector pEG1297 had been constructed by ligating the 3.1 kb EcoRI fragment of the *Bacillus* pNN101 (Norton et al., 1985) into NdeI digested pUC18. pEG1297 is capable of replication in both *E. coli* and *B. thuringiensis* and confers $Amp^R$ to *E. coli* and tetracycline (Tet) resistance ($Tet^R$) to *B. thuringiensis*. The two ligation mixtures were first introduced into *E. coli* DH5α™ cells by transformation procedures described by the manufacturers (Gibco-BRL, Gaithersburg, Md.). Plasmid DNA was prepared from $Amp^R$ transformants and restriction enzyme analysis was performed to confirm the proper construction. The plasmid consisting of the 5-kb EcoRI fragment of pEG1298 inserted into pEG1297 was designated pEG1302. The plasmid consisting of the 7-kb EcoRI fragment of pEG1299 inserted into pEG1297 was designated pEG1303.

pEG1302 and pEG1303 were separately introduced into a Cry⁻ *B. thuringiensis* strain, EG10368, by electroporation (Macaluso and Mettus, 1991). Cells transformed to tetracycline resistance were selected by incubation overnight on LB agar plates containing 10 μg/ml Tet. One $Tet^R$ colony from each transformation was selected for further analysis. Recombinant strain EG11494 contains pEG1302 (NRRL B-21583) and recombinant strain EG11502 contains pEG1303.

EG11494 and EG11502 were grown in C2 sporulation medium containing 10 μg/ml tetracycline for 3 days at 30° C. until sporulation and cell lysis had occurred. Microscopic examination of the sporulated cultures demonstrated that the recombinant strains were producing small crystalline inclusions. These crystals resemble the crystals produced by the wild-type strain EG4096, indicating that the cryET29 gene in each recombinant was a functional gene capable of directing the expression of the CryET29 protein.

The sporulated cultures of EG11494 and EG11502 were harvested by centrifugation, washed, and resuspended in 0.005% Triton X-100® in one-tenth the original volume. The crystal protein in the suspensions was characterized by SDS-PAGE analysis which revealed the production of an approximately 25-kDa protein by both EG11494 and EG11502. The 25-kDa proteins produced by the recombinant strains are identical in size as determined by migration on an SDS gel, to the crystal protein of EG4096.

The amount of toxin protein contained in a particular sample was quantified for insect bioassays by SDS-PAGE. The Coomassie stained SDS-PAGE gel was scanned on a densitometer and compared with a standard curve generated by loading known amounts of a protein, such as bovine serum albumin, on the same gel.

5.8 Example 8

Toxicity of CryET29 to Southern Corn Rootworm Larvae

The toxicity to southern corn rootworm (SCRW) larvae (*Diabrotica undecimpunctata howardi*) was determined for wild-type *B. thuringiensis* EG4096 and for the two recombinant strains expressing the CryET29 protein, EG11494 and EG11502.

EG4096, EG11494, and EG11502 were grown in C2 medium at 30° C. for 3 days until sporulation and cell lysis had occurred. The cultures were harvested by centrifugation, washed twice in 1× original volume 0.005% Triton X-100®, and resuspended in ¹⁄₁₀ the original culture volume on 0.005% Triton X-100®. For comparison, a recombinant *B. thuringiensis* strain, EG 11535, expressing the coleopteran-toxic protein CryIIIB2 (Donovan et al., 1992), was grown and harvested in the same manner.

SCRW larvae were bioassayed via surface contamination of an artificial diet similar to Marrone et al. (1985), but without formalin. Each bioassay consisted of eight serial aqueous dilutions with aliquots applied to the surface of the diet. After the diluent (an aqueous 0.005% Triton X-100® solution) had dried, first instar larvae were placed on the diet and incubated at 28° C. Thirty-two larvae were tested per dose. Mortality was scored after 7 days. Data from replicated bioassays were pooled for probit analysis (Daum, 1970) with mortality being corrected for control death, the control being diluent only (Abbot, 1925). Results are reported as the amount of CryET29 crystal protein per well (175 mm² of diet surface) resulting in an $LC_{50}$, the concentration killing 50% of the test insects. 95% confidence intervals are also reported (Table 5).

TABLE 5

Insecticidal Activity of the CryET29 Protein to SCRW Larvae

| Sample | $LC_{50}$ (μg protein/well) | 95% C.I. |
|---|---|---|
| EG4096 | 35.3 | 29-43 |
| EG11494 | 24.3 | 20-30 |
| EG11502 | 26.7 | 22-32 |
| EG11535 (CryIIIB2) | 17.8 | 14-23 |

The results shown in Table 5 demonstrate that the CryET29 protein has significant activity on larvae of the southern corn rootworm. The CryET29 produced by the two recombinant strains, EG11494 and EG11502, also exhibit significant toxicity. The SCRW activity of the CryET29 protein produced in EG 11494 and EG11502 is somewhat lower than that seen for the CryIIIB2 protein, although the 95% confidence intervals do overlap slightly, indicating that the difference may not be significant.

5.9 Example 9

Toxicity of CryET29 to Western Corn Rootworm Larvae

The toxicity to western corn rootworm (WCRW) larvae (*Diabrotica virgifera virgifera*) was determined for wild-type *B. thuringiensis* EG4096 and for the two recombinant strains expressing the CryET29 protein, EG11494 and EG11502.

The samples were prepared and the bioassays performed essentially as described for the SCRW assays in Example 8. The wild-type *B. thuringiensis* strain EG4961, which produces the Coleopteran-active CryIIIB2 protein, was included in the assay as a positive control (Table 6).

TABLE 6

Insecticidal Activity of the CryET29 Protein to SCRW Larvae

| Sample | $LC_{50}$ (µg protein/well) | 95% C.I. |
| --- | --- | --- |
| EG4961 (CryIIIB2) | 73.8 | 44-211 |
| EG4096 | 12.9 | 7-110 |
| EG11494 | 8.7 | 4-19 |
| EG11502 | 13.9 | 9-29 |

The results in Table 6 demonstrate that the CryET29 protein has significant activity on larvae of the WCRW. Furthermore, the activity of the CryET29 produced by the recombinant strains EG11494 and EG11502 have significantly higher activity (i.e., lower $LC_{50}$s) than the protein produced by the coleopteran-active *B. thuringiensis* strain EG4096961.

5.10 Example 10

Toxicity of CryET29 to Colorado Potato Beetle Larvae

The toxicity to Colorado potato beetle (CPB) (*Leptinotarsa decemlineata*) larvae was determined for the wild-type *B. thuringiensis* strain EG4096 and for the recombinant strain expressing the CryET29 protein, EG11494. The recombinant strain EG7231, which expresses the CryIIIB2 protein, was grown for purposes of comparison.

The assay on CPB larvae was performed using similar techniques to the SCRW assay, except for the substitution of BioServe's #9380 insect diet (with potato flakes added) for the artificial diet. Mortality was scored at three days instead of seven days. For this assay 16 insects were used per dose (Table 7).

TABLE 7

Percent Mortality of CPB Larvae Treated With CryET29-Producing Strains

| Dose in µg/well | EG4096 | EG11494 | EG7231 (CryIIIB2) |
| --- | --- | --- | --- |
| 4.375 | 100 | 68.75 | |
| 8.75 | 100 | 75 | |
| 9.375 | | | 100 |
| 17.5 | 100 | 75 | |
| 35 | 100 | 93 | |

The results shown in Table 7 demonstrate the insecticidal activity of the CryET29 protein on CPB larvae.

5.11 Example 11

Toxicity of *B. thuringiensis* EG4096 to Red Flour Beetle Larvae

Toxicity of EG4096 to red flour beetle larvae (*Tribolium castaneum*) was determined by applying a washed and concentrated sporulated culture of EG4096 to an artificial diet and allowing the larvae to feed on the diet. Sixteen larvae were treated in this manner and the percent mortality was scored after two weeks. Larvae treated with the EG4096 suspension exhibited 44% mortality compared to 13% for the untreated check. In addition the surviving larvae treated with EG4096 exhibited significant stunting in their growth which is indicative of a sublethal dose of an active toxin. The larvae in the untreated check showed no such stunting. These results demonstrate that EG4096, which produces the CryET29 protein, is toxic to red flour beetle.

5.12 Example 12

Toxicity of *B. thuringiensis* EG4096 to Japanese Beetle Larvae

The toxicity to Japanese beetle (JB) larvae (*Popillia japonica*) was determined for *B. thuringiensis* EG4096, which produces the CryET29 protein. Freeze-dried powders were prepared from washed and concentrated sporulated cultures of EG4096. The amount of CryET29 protein present in the sample was determined by SDS-PAGE and quantitative densitometry of the Coomassie stained gels.

The freeze-dried powders were resuspended in a diluent containing 0.005% Triton X-100® and incorporated into 100 ml of hot (50-60° C.) liquid artificial diet (based on the insect diet described by Ladd (1986). The mixtures were allowed to solidify in Petri dishes, and 19-mm diameter plugs of the solidified diet were placed into ⅝ ounce plastic cups. One JB larva was introduced per cup which were then covered with a lid and held at 25° C. for fourteen days before larval mortality was scored.

Table 8 shows the average of results from two replications of the bioassay using 20 larvae per replication. The dosages were based on the amount of CryET29 protein in the sample. Percent mortality was corrected according to Abbott (1925).

TABLE 8

Toxicity of EG4096 to Japanese Beetle Larvae

| Amount CryET29 (ppm) | % Mortality |
| --- | --- |
| 250 ppm | 9 |
| 500 ppm | 69 |
| 1000 ppm | 92 |
| 2000 ppm | 96 |

The results shown in Table 8 demonstrate that the CryET29 protein produced by EG4096 has significant insecticidal activity on JB larvae.

5.13 Example 13

Toxicity of *B. thuringiensis* EG4096 to Cat Flea Larvae

The toxicity to larvae of the cat flea (*Ctenocephalides felis*) was determined for *B. thuringiensis* EG4096, which produces the CryET29 protein. Freeze-dried powders were prepared from washed and concentrated sporulated cultures of EG4096. The amount of CryET29 protein present in the sample was determined by SDS-PAGE.

To perform the bioassay an amount of the freeze-dried powder containing 1 mg of CryET29 protein was mixed with 1 gram of dried bovine blood resulting in a concentration of 1000 ppm. The mixture was suspended in 0.1% Triton X-100® and poured into a glass Petri dish to dry. The dried sample was then ground into a fine powder and evenly distributed into 32 bioassay wells. One cat flea larva was added to each well which was then covered with a lid and kept at high humidity. The assays were then scored after seven days.

The assay is performed in this manner using a powder of EG4096 as the sample and the results are shown in Table 9. Thirty-two larvae were assayed at each dose. Percent mortality was scored after 1, 4, and 7 days. A *B. thuringiensis* strain that does not produce a toxin protein, EG2205, was used to assess control mortality.

TABLE 9

Toxicity of EG4096 to First Instar Cat Flea Larvae

| | | % Mortality | | |
|---|---|---|---|---|
| Strain | CryET29 (ppm) | 1 Day | 4 Day | 7 Day |
| EG4096 | 500 | 6.25 | 15.60 | 15.60 |
| EG4096 | 1000 | 9.40 | 34.40 | 43.75 |
| EG4096 | 5000 | 46.90 | 78.10 | 87.50 |
| EG4096 | 10000 | 84.40 | 93.75 | 100.00 |
| EG2205 | No toxin | 3.10 | 15.60 | 15.60 |

The results shown in Table 9 demonstrate that the CryET29 protein produced by *Bacillus thuringiensis* strain EG4096 has significant insecticidal activity on larvae of the cat flea, *Ctenocephalides felis.*

The uniqueness of the activity of the CryET29 toxin on cat fleas larvae was demonstrated by assaying other *Bacillus thuringiensis* insecticidal crystal proteins in the manner described above. Samples containing spores and crystals were tested from recombinant strains of *B. thuringiensis* expressing the following toxin proteins: Cry1Aa, Cry1Ab, Cry1Ac, Cry2S, Cry3A, Cry3B, Cry3B2, and Cry3B3. The characteristics of these other classes of insecticidal crystal protein genes are described by Hofte et al., (1989). For a detailed description of the Cry3 toxins, see U.S. Pat. No. 5,187,091 and U.S. Patent No. 5,264,364, specifically incorporated herein by reference. None of these toxins showed any toxicity toward the larvae of the cat flea indicating that the CryET29 toxin protein is unique among *B. thuringiensis* insecticidal proteins isolated to date with respect to its cat flea larvae toxicity.

6. REFERENCES

The following references, to the extent that they provide exemplary procedural or other details supplementary to those set forth herein, are specifically incorporated herein by reference.

U.S. Pat. No. 4,008,688, issued Feb. 22, 1977.
U.S. Pat. No. 4,196,265, issued Apr. 1, 1980.
U.S. Pat. No. 4,547,360, issued Oct. 15, 1985.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,702,914, issued Oct. 27, 1987.
U.S. Pat. No. 4,757,011, issued Jul. 12, 1988.
U.S. Pat. No. 4,769,061, issued Sep. 6, 1988.
U.S. Pat. No. 4,940,835, issued Feb. 23, 1990.
U.S. Pat. No. 4,965,188, issued Oct. 23, 1990.
U.S. Pat. No. 4,971,908, issued Nov. 20, 1990.
U.S. Pat. No. 5,176,995, issued Oct. 15, 1991.
U.S. Pat. No. 5,187,091, issued Feb. 16, 1993.
U.S. Pat. No. 5,225,341, issued Jul. 6, 1993.
U.S. Pat. No. 5,264,364, issued Nov. 23, 1993.
U.S. Pat. No. 5,276,269, issued Jan. 4, 1994.
U.S. Pat. No. 5,384,253, issued Jan. 24, 1995.
U.S. Pat. No. 5,416,102, issued May 16, 1995.
U.S. Pat. No. 5,449,681, issued Sep. 12, 1995.
U.S. Pat. No. 5,482,852, issued Jan. 9, 1996.
U.S. Pat. No. 5,508,468, issued Apr. 16, 1996.
U.S. Pat. No. 5,550,318, issued Aug. 27, 1996.
Intl. Pat. Appl. Publ. No. WO 95/02693, published Jan. 26, 1995.
Abbot, W. S., *J. Econ. Entomol.,* 18:265-267, 1925.
Abdullah et al., *Biotechnology,* 4:1087, 1986.
Altschul et al., "Basic local alignment search tool," *J. Mol. Biol.,* 215:403-410, 1990.
Baum, J. A., and T. Malvar, "Regulation of insecticidal crystal protein production in *Bacillus thuringiensis,*" *Molec. Microbiol.,* 18(1): 1-12.
Benbrook et al., *In: Proceedings Bio Expo* 1986, Butterworth, Stoneham, Mass., pp. 27-54, 1986.
Bytebier et al., *Proc. Natl. Acad. Sci. USA,* 84:5345, 1987.
Callis et al., *Genes and Development,* 1:1183, 1987.
Campbell, "Monoclonal Antibody Technology, Laboratory Techniques in Biochemistry and Molecular Biology," Vol. 13, Burden and Von Knippenberg, Eds. pp. 75-83, Elsevier, Amsterdam, 1984.
Capecchi, M. R., "High efficiency transformation by direct microinjection of DNA into cultured mammalian cells," *Cell* 22(2):479-488, 1980.
Carlton and Gonzalez, In: *Molecular Biology of Microbial Differentiation*, J. A. Hoch and P. Setlow, ed., American Society for Microbiology, Washington, D.C., pp. 246-252, 1985.
Cashmore et al., *Gen. Eng. of Plants*, Polonium Press, New York, 29-38, 1983.
Chau et al., *Science,* 244:174-181, 1989.
Chilcott, C. N., and Ellar, D. J., *J. Gen. Microbiol.,* 134:2551-2558, 1988.
Clapp, D. W., "Somatic gene therapy into hematopoietic cells. Current status and future implications," *Clin. Perinatol.* 20(1):155-168, 1993.
Cristou et al., *Plant Physiol,* 87:671-674, 1988.
Curiel, D. T., Agarwal, S., Wagner, E., and Cotten, M., "Adenovirus enhancement of transferrin-polylysine-mediated gene delivery," *Proc. Natl. Acad. Sci. USA* 88(19):8850-8854, 1991.
Curiel, D. T., Wagner, E., and Cotten, M., Bimstiel, M. L., Agarwal, S., Li, C. M., Loechel, S., and Hu, P. C. high-efficiency gene transfer mediated by adenovirus coupled to DNA-polylysine complexes," *Hum. Gen. Ther.* 3(2):147-154, 1992.
Daum, R. J., *Bull. Entomol. Soc. Am.,* 15:10-15, 1970.
Dhir et al., *Plant Cell Reports,* 10:97, 1991.
Donovan et al., *Appl. Environ. Microbiol.,* 58:3921-3927, 1992.
Earp, D. J. and Ellar, D. J., *Nucl. Acids Res.,* 15:3619, 1987.
Eglitis, M. A., and Anderson, W. F., "Retroviral vectors for introduction of genes into mammalian cells," *Biotechniques* 6(7):608-614, 1988(a).
Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Adv. Exp. Med. Biol.* 241:19-27, 1988(b). Fraley et al., *Proc. Natl. Acad. Sci. USA*, 80:4803, 1983.
Fraley et al., *Proc. Natl., Acad. Sci. USA*, 80:4803, 1983.
Fraley et al., *Biotechnology*, 3:629, 1985.
Fromm, M., Taylor, L. P., and Walbot, V., "Expression of genes transferred into monocot and dicot plant cells by electroporation," *Proc. Natl. Acad. Sci. USA* 82(17): 5824-5828, 1985.
Fujimura et al., *Plant Tissue Culture Letters*, 2:74, 1985.
Fynan, E. F., Webster, R. G., Fuller, D. H., Haynes, J. R., Santoro, J. C., and Robinson, H. L., "DNA vaccines: protective immunizations by parenteral, mucosal, and gene gun inoculations," *Proc. Natl. Acad. Sci. USA* 90(24): 11478-11482, 1993.
Gefter et al., *Somatic Cell Genet.* 3:231-236, 1977.
Goding, "Monoclonal Antibodies: Principles and Practice," pp. 60-74. 2nd Edition, Academic Press, Orlando, Fla., 1986.
Gonzalez, Jr. et al., *Proc. Natl. Acad. Sci. USA*, 79:6951-6955, 1982.
Graham, F. L., and van der Eb, A. J., "Transformation of rat cells by DNA of human adenovirus 5," *Virology* 54(2):536-539, 1973.
Harlow, E. and Lane, D. "Antibodies: A Laboratory Manual," Cold Spring Harbor Laboratory, Cold Spring Harbor, N.Y., 1988.
Hess, *Intern Rev. Cytol.*, 107:367, 1987.
Hofte et al., *Microbiol. Rev.*, 53:242-255, 1989.
Jameson and Wolf, *Compu. Appl. Biosci.*, 4(1):181-6, 1988.
Johnston, S. A., and Tang, D. C., "Gene gun transfection of animal cells and genetic immunization," *Methods Cell. Biol.* 43(A):353-365, 1994.
Jorgensen et al., *Mol. Gen. Genet.*, 207:471, 1987.
Keller et al, *EMBO J.*, 8:1309-14, 1989.
Klein et al., *Nature*, 327:70, 1987.
Klein et al., *Proc. Natl. Acad. Sci. USA*, 85:8502-8505, 1988.
Kohler and Milstein, *Eur. J. Imnunol.* 6:511-519, 1976.
Kohler and Milstein, *Nature* 256:495-497, 1975.
Knowles et al., *Proc. Royal Soc. London*, 248:1-7, 1992.
Koni, P. A. and Ellar, D. J., *J. Mol. Biol.*, 229:319-327, 1993.
Korn, L. J. and Queen, C., "Analysis of Biological Sequences on Small Computers" *DNA*, 3:421-436, 1984.
Kuby, J., *Immunology* 2nd Edition, W. H. Freeman & Company, NY, 1994
Kyte and Doolittle, *J. Mol. Biol.*, 157:105-132, 1982.
Ladd, Jr., *J. Econ. Entomol.*, 79:668-671, 1986.
Langridge et al., *Proc. Natl. Acad. Sci. USA*, 86:3219-3223, 1989.
Lindstrom et al., *Developmental Genetics*, 11: 160, 1990.
Lorz et al., *Mol. Gen. Genet.*, 199:178, 1985.
Lu, L., Xiao, M., Clapp, D. W., Li, Z. H., and Broxmeyer, H. E., "High efficiency retroviral mediated gene transduction into single isolated immature and replatable CD34(3+) hematopoietic stem/progenitor cells from human umbilical cord blood," *J. Exp. Med.* 178(6):2089-2096, 1993.
Luo et al., *Plant Mol. Biol. Reporter*, 6:165, 1988.
Macaluso, A. and Mettus, A-M., *J. Bacteriol.*, 173:1353-1356, 1991.
Maddock et al., *Third International Congress of Plant Molecular Biology*, Abstract 372, 1991.
Maloy et al., "Microbial Genetics" 2nd Edition. Jones and Barlett Publishers, Boston, Mass., 1994.
Marcotte et al., *Nature*, 335:454, 1988.
Marrone et al., *J. Econ. Entomol.*, 78:290-293, 1985.
McCabe et al., *Biotechnology*, 6:923, 1988.
Neuhaus et al., *Theor. Appl. Genet.*, 75:30, 1987.
Norton et al., *Plasmid*, 13:211-214, 1985.
Odell et al., *Nature*, 313:810, 1985.
Omirulleh et al., *Plant Molecular Biology*, 21:415-428, 1993.
Pena et al., *Nature*, 325:274, 1987.
Poszkowski et al., *EMBO J.*, 3:2719, 1989.
Potrykus et al., *Mol. Gen. Genet.*, 199:183, 1985.
Poulsen et al., *Mol. Gen. Genet.*, 205:193-200, 1986.
Prokop, A., Bajpai, R. K., *Ann. N.Y. Acad. Sci.* 646, 1991
Rogers et al., *Meth. in Enzymol.*, 153:253-277, 1987.
Rogers et al., *In: Methods For Plant Molecular Biology*, A. Weissbach and H. Weissbach, eds., Academic Press Inc., San Diego, Calif. 1988.
Sambrook et al., "Molecular Cloning: A Laboratory Manual," Cold Spring Harbor Laboratory, Cold Spring Harbor, N.Y., 1989.
Sanger et al., *Proc. Natl. Acad. Sci. USA*, 74:5463-5467, 1977.
Segal, I. H., "Biochemical Calculations" 2nd Edition. John Wiley & Sons, New York, 1976.
Simpson, *Science*, 233:34, 1986.
Southern, E. M., *J. Mol. Biol.*, 98:503-517, 1975.
Spielmann et al., *Mol. Gen. Genet.*, 205:34, 1986.
Toriyama et al., *Theor Appl. Genet.*, 73:16, 1986.
Uchimiya et al., *Mol. Gen. Genet.*, 204:204, 1986.
Van Tunen et al., *EMBO J.*, 7:1257, 1988.
Vasil, *Biotechnology*, 6:397, 1988.
Vasil et al., "Herbicide-resistant fertile transgenic wheat plants obtained by microprojectile bombardment of regenerable embryogenic callus," *Biotechnology*, 10:667-674, 1992.
Vodkin et al., *Cell*, 34:1023, 1983.
Vogel et al., *J. Cell Biochem.*, supplement 13D:312, 1989.
Ward et al., *FEBS Lett.*, 175:377-382, 1984.
Ward, E. S. and Ellar, D. J., *J. Mol. Biol.*, 191:1-11, 1986.
Weissbach and Weissbach, *Methods for Plant Molecular Biology*, (eds.), Academic Press, Inc., San Diego, Calif., 1988.
Wenzler et al., *Plant Mol. Biol.*, 12:41-50, 1989.
Wolf et al., *Compu. Appl. Biosci.*, 4(1):187-91 1988.
Wong, T. E., and Neumann, E., "Electric field mediated gene transfer," *Biochim. Biophys. Res. Commun.* 107(2):584-587, 1982.
Yaniada et al., *Plant Cell Rep.*, 4:85, 1986.
Yang et al., *Proc. Natl. Acad. Sci. USA*, 87:4144-48, 1990.
Yanisch-Perron et al., *Gene*, 33:103, 1985.
Zatloukal, L., Wagner, E., Cotten, M., Phillips, S., Plank, C., Steinlein, P., Curiel, D. T., and Bimstiel, M. L., "Transferrinfection: a highly efficient way to express gene constructs in eukaryotic cells," *Ann. N.Y. Acad. Sci.*, 660:136-153, 1992.
Zhou et al., *Methods in Enzymology*, 101:433, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. An isolated nucleic acid segment characterized as:
   (a) a nucleic acid segment consisting of at least 30 nucleotides that has the same sequence as, or is fully complementary to, 30 contiguous nucleotides of SEQ ID NO:1; or
   (b) a nucleic acid segment consisting of at least 30 nucleotides that specifically hybridizes to SEQ ID NO:1 or the full complement thereof under stringent conditions for high selectivity comprising 0.02 M to 0.15 M NaCl at temperatures of about 50° C. to about 70° C.

2. The isolated nucleic acid segment of claim 1 consisting of the sequence as set forth in SEQ ID NO:4.

3. The isolated nucleic acid segment of claim 1 comprising the sequence as set forth in SEQ ID NO:4.

4. A method for detecting a nucleic acid sequence encoding a Coleopteran toxic crystal protein, comprising the steps of:
   (a) obtaining sample nucleic acids suspected of encoding a Coleopteran toxic crystal protein;
   (b) contacting said sample nucleic acids with the isolated nucleic acid segment of claim 1, 2 or 3 under conditions effective to allow hybridization of complementary nucleic acids; and
   (c) detecting the hybridized complementary nucleic acids thus formed.

5. The method of claim 4, wherein said nucleic acid segment comprises a detectable label and said hybridized complementary nucleic acids are detected by detecting said label.

6. A nucleic acid detection kit comprising, in suitable container means, the nucleic acid segment of claim 1, 2 or 3 and a detection reagent.

* * * * *